United States Patent [19]

Kuhn et al.

[11] 3,963,834

[45] June 15, 1976

[54] PHARMACEUTICAL COMPOSITIONS FOR THE TREATMENT OF HYDROPIC CONDITIONS

[75] Inventors: Rolf Kuhn, Manheim-Waldhof; Klaus Hardebeck, Ludwigshafen (Rhine); Helmut Heinemann, Heidelberg; Knut Osmers, Viernheim, all of Germany

[73] Assignee: Boehringer Mannheim G.m.b.H., Mannheim-Waldorf, Germany

[22] Filed: Apr. 18, 1975

[21] Appl. No.: 569,635

[30] Foreign Application Priority Data

May 15, 1974 Germany............................ 2423550

[52] U.S. Cl. ................................................ 424/240
[51] Int. Cl.² ........................................... A61K 31/56
[58] Field of Search ................................... 424/240

[56] References Cited
FOREIGN PATENTS OR APPLICATIONS 17,77M 4/1963 France............................... 424/240

*Primary Examiner*—Ethel G. Love
*Attorney, Agent, or Firm*—Burgess, Dinklage & Sprung

[57] ABSTRACT

Pharmaceutical compositions comprising
a. at least one member of the group consiting of 5-(4-chloro-5-sulfamoyl-2-thenylaminophenyl)-tetrazole and the pharmacologically compatible salts thereof
b. at least one member of the group consisting of 3-(3-oxo-17$\beta$-hydroxy-4,6-androstadien-17$\alpha$-yl)-propionic acid-$\gamma$-lactone and the pharmacologically compatible salts of 3-(3-oxo-17$\beta$-hydoxy-4,6-androstadien-17$\alpha$-yl)-propionic acid, and a pharmaceutical carrier;

possess outstanding activity for treating hydropic conditions and prevent undesirable increased excretion of potassium without at the same time impairing the desired excretion of water and sodium.

24 Claims, No Drawings

PHARMACEUTICAL COMPOSITIONS FOR THE TREATMENT OF HYDROPIC CONDITIONS

The present invention relates to a pharmaceutical composition for the treatment of various hydropic conditions.

When using 5-(4-chloro-5-sulfamoyl-2-thenylaminophenyl)-tetrazole for the treatment of various hydropic conditions, for example cirrhosis of the liver, cardiac insufficiency, cor pulmonale, respiratory insufficiency, water retention in case of chronic kidney diseases and hydropic conditions of patients with neoplasms, the pathologically accumulated water, together with excess mineral salts, can be excreted quickly and effectively.

However, when using this active material, an increased excretion of potassium is frequently observed which can result in a reduction of the potassium content of the body cells, as well as of the blood. This results in disturbances of the actions of the cardiac and skeletal muscles, as well as in metabolic changes, especially in the metabolism of carbohydrates.

It has now been found that, in accordance with the present invention, it is possible to prevent such increased excretion of potassium without, at the same time, impairing the excretion of water and sodium.

Surprisingly, we have now found that the simultaneous administration of 3-(3-oxo-17β-hydroxy-4,6-androstadien-17α-yl-propionic acid-γ-lactone and/or at least one pharmacologically compatible salt of 3-(3-oxo-17β-hydroxy-4,6-androstadien-17α-yl)-propionic acid, which themselves have a diuretic action, can normalize the increased excretion of potassium brought about by 5-(4-chloro-5-sulfamoyl-2-thenylaminophenyl)-tetrazole.

This finding is very surprising since the combined action of the active materials 5-(4-chloro-5-sulfamoyl-2-thenylaminophenyl)-tetrazole and 3-(3-oxo-17β-hydroxy-4,6-androstadien-17α-yl)-propionic acid-γ-lactone and/or salts of 3-(3-oxo-17β-hydroxy-4,6-androstadien-17α-yl)-propionic acid admittedly increases the excretion of water and sodium but, at the same time, normalizes the excretion of potassium. Thus, by the combination according to the present invention, the necessary excretion of water and sodium is further increased and, at the same time, the potassium level of the skeletal and cardiac muscle, as well as of the blood, can be maintained at the desired level.

Analogous results are obtained when using the salts of 5-(4-chloro-5-sulfamoyl-2-thenylaminophenyl)-tetrazole.

Of the salts of 3-(3-oxo-17β-hydroxy-4,6-androstadien-17α-yl)-propionic acid, the potassium salt is particularly preferred.

Thus, the present invention provides a pharmaceutical composition comprising 5-(4-chloro-5-sulfamoyl-2-thenylaminophenyl)-tetrazole and/or at least one pharmacologically compatible salt thereof and 3-(3-oxo-17β-hydroxy-4,6-androstadien-17α-yl)-propionic acid-γ-lactone and/or at least one pharmacologically compatible salt of 3-(3-oxo-17β-hydroxy-4,6-androstadien-17α-yl)-propionic acid, together with a pharmaceutical diluent or carrier.

5-(4-Chloro-5-sulfamoyl-2-thenylaminophenyl)-tetrazole and the pharmacologically compatible salts thereof are described in U.S. Pat. No. 3,665,002.

3-(3-Oxo-17β-hydroxy-4,6-androstadien-17α-yl)-propionic acid-γ-lactone, as well as the salts of 3-(3-oxo-17β-hydroxy-4,6-androstadien-17α-yl)-propionic acid, are described in U.S. Pat. No. 2,900,383 and in French Pat. No. 85 CAM/No. 511 M.

The pharmaceutical composition of the present invention can be used for the treatment of severe hydropic conditions, especially of a chronic nature, such as cirrhosis of the liver, cardiac insufficiency, cor pulmonale, respiratory insufficiency, chronic diseases of the kidneys. The pharmaceutical composition according to the present invention is especially suitable when, due to the causes of the disease to be treated, prolonged therapy is unavoidable.

The above-mentioned active materials are preferably present in the new composition in such amounts that for 41 parts by weight of 3-(3-oxo-17β-hydroxy-4,6-androstadien-17α-yl)-propionic acid-γ-lactone, there are present 10 to 100 parts and especially 15 to 30 parts by weight of 5-(4-chloro-5-sulfamoyl-2-thenylaminophenyl)-tetrazole.

In the case of injection forms of the new composition, per 200 parts by weight of a salt of 3-(3-oxo-17β-hydroxy-4,6-androstadien-17α-yl)-propionic acid, there are preferably present 10 to 50 parts and especially 15 to 30 parts by weight of 5-(4-chloro-5-sulfamoyl-2-thenylaminophenyl)-tetrazole.

The daily dosage is preferably about 40 to 400 mg. and especially 56 to 300 mg. of the active material combination. The daily dosage can be taken in the morning or can be spread out over the day in the form of 3 individual doses.

The composition according to the present invention can be in any of the conventional forms for oral or parenteral administration, for example, tablets, capsules, dragees, syrup solutions, suspensions, drops, suppositories and the like. For this purpose, the active materials are mixed with solid or liquid carrier materials and subsequently brought into the desired form. Examples of solid carrier materials include lactose, mannitol, starch, talc, methyl cellulose, magnesium stearate and gelatine, to which, if desired, coloring and/or flavoring materials can be added. Liquid carrier materials for injection solutions must be sterile and pyrogen-free and are preferably placed into ampules.

The composition according to the present invention is preferably administered in the form of a tablet or capsule.

The following Examples are given for the purpose of illustrating the present invention. For the sake of brevity, 3-(3-oxo-17β-hydroxy-4,6-androstadien-17α-yl)-propionic acid-γ-lactone is referred to as Compound A, 5-(4-chloro-5-sulfamoyl-2-thenylaminophenyl)-tetrazole (powdered) as Compound B and 3-(3-oxo-17β-hydroxy-4,6-androstadien-17α-yl)-propionic acid as Compound C:

EXAMPLE 1

| | |
|---|---|
| Compound A | 820.0 g. |
| lactose (DAB) | 820.0 g. | were mixed together and micronized. The mixture was then mixed with

| | |
|---|---|
| lactose (DAB) | 3260.0 g. |
| microcrystalline cellulose | 750.0 g. |
| highly dispersed silicic acid | 2.0 | and granulated, in known manner, with an aqueous solution of

| | |
|---|---|
| polyoxyethylene stearate | 328.0 g. | and the granulate obtained was dried and sieved. This dried granulate was mixed with

| | |
|---|---|
| Compound B | 300.0 g. |
| corn starch (DAB) | 80.0 g. |
| magnesium stearate (USP) | 40.0 g. |

The active material-containing mixture can be filled into hard gelatine capsules or can be pressed into tablets so that, in the case of a total weight of 320 mg., each dosage unit form contains 41 mg. of Compound A and 15 mg. of Compound B. The tablets are preferably coated in known manner.

EXAMPLE 2

Two-layer tablets
1st Layer

| | |
|---|---|
| Compound A | 820.0 g. |
| lactose (DAB) | 820.0 g. | were mixed together and micronized. The mixture was then mixed with

| | |
|---|---|
| lactose (DAB) | 1200.0 g. |
| corn starch (DAB) | 1200.0 g. |
| highly dispersed silicic acid | 40.0 g. | and granulated in known manner with an aqueous solution of

| | |
|---|---|
| polyoxyethylene stearate | 300.0 g. | and the granulate dried and sieved. The granulate was mixed with

| | |
|---|---|
| magnesium stearate (USP) | 20.0 g. |

This active material-containing mixture was used as the first layer of 220 mg. weight, containing 41 mg. of Compound A.

| 2nd Layer | |
|---|---|
| Compound B | 600.0 g. |
| lactose (DAB) | 780.0 g. |
| corn starch (DAB) | 600.0 g. | were mixed together and granulated with an aqueous slurry of

| | |
|---|---|
| corn starch (DAB) | 80.0 g. | and the granulate was dried and sieved and then mixed with

| | |
|---|---|
| microcrystalline cellulose | 400.0 g. |
| sodium carboxymethylamylopectin | 120.0 g. |
| magnesium stearate (USP) | 20.0 g. |

This mixture was used as the second layer with a weight of 130 mg., containing 30 mg. of Compound B.

The two-layer tablet was produced in tabletting machines which are suitable for this purpose. The tablets obtained were preferably coated in known manner.

EXAMPLE 3

For the preparation of an injectable form of the composition, 186.0 g. of Compound C were suspended in 1.5 liters of water suitable for injection purposes and, by the addition of a 10% aqueous solution of potassium hydroxide, dissolved at pH 10.6–11.0, with the formation of the potassium salt of Compound C. 15.0 g. of Compound B were added to the solution and the pH again adjusted to 10.6–11.0. Subsequently, 72.0 g. 2-amino-2-(hydroxy-methyl)-propane-1,3-diol were added thereto and the solution made up to 2 liters with water suitable for injection purposes. After an appropriate sterilizing filtration, the solution was filled in 2.0 ml. amounts into brown 20 ml. injection flasks and then lyophilized in known manner. The lyophilizate contained, per injection flask, 200.0 mg. of the potassium salt of Compound C and 15.0 mg. of Compound B. For administration to a patient, the lyophilizate was dissolved by the addition of 20 ml. water suitable for injection purposes.

EXAMPLE 4

A lyophilizate was prepared in the manner described in Example 3 from 186.0 g. Compound C, 30.0 g. of Compound B and 72.0 g. 2-amino-2-(hydroxymethyl)-propane-1,3-diol, with addition of water and of an aqueous solution of potassium hydroxide so that the lyophilizate obtained contained, per injection flask, 200.0 mg. of the potassium salt of Compound C and 30.0 mg. of Compound B.

The compounds of this invention possess outstanding diuretic and saluretic properties. In order to establish the effectiveness of compounds representative of this invention as therapeutic agents for diuretic and saluretic purposes, the following series of tests were carried out.

The test animals were female Sprague-Dawley rats each weighing between 170–220 grams. The test animals were kept in climate controlled rooms at $23°\pm 1°C$. and a relative humidity of $60 \pm 5$ percent for at least 1 week prior to the tests. On the evening prior to the test day (i.e., 16 hours prior to administration of test compounds), the rats were left without food and had access only to drinking water. During the tests, groups of 5 animals each were placed into metabolic cages and six such groups of animals were used in the tests. The test compounds were administered to the test animals as a suspension in 1% methyl cellulose at the rate of 10 milliliters per kg. of body weight of each rat. The test preparations were administered per os. The dosage in terms of milligrams of test compounds per kg. of body weight is set forth in Table 1 below. Prior to the test and ater 6 hours subsequent to the test, the bladders of the rat were emptied by squeezing, the urine content was measured, the chloride content in the urine was determined by titration, and sodium and potassium were determined by flame photometric tests.

The results are set forth in Table 1 below, wherein the test compounds were again designated as follows:

5-(4-Chloro-5-sulfamoyl-2-thenyl-aminophenyl)-tetrazole: Compound B 3-(3-Oxo-17β-hydroxy-4,6-androstadien-17α-yl)-propionic acid (Canrenon): Compound C.

TABLE 1

DIURETIC EFFECTIVENESS IN PER
OS ADMINISTRATION IN RATS
(Test compounds in 1% methyl cellulose suspension)

| Test compound | Dosage (mg/kg) | Separation/kg. during 0 – 6 hours | | |
|---|---|---|---|---|
| | | Na⁺ | K⁺ | Na/K |
| Control | — | 0.486 ±0.053 | 0.454 ±0.041 | 1.07 ±0.08 |
| Compound B | 25 | 0.448 ±0.07 | 0.406 ±0.04 | 1.08 ±0.15 |
| Compound B | 50 | 2.38 ±0.32 | 1.071 ±0.06 | 2.18 ±0.2 |
| Compound C | 41 | 0.782 ±0.05 | 0.155 ±0.02 | 5.25 ±0.39 |
| Compounds B and C | 25 +41 | 0.864 ±0.036 | 0.187 ±0.021 | 4.62 ±0.24 |
| Compounds B and C | 50 +41 | 1.69 ±0.042 | 0.362 ±0.023 | 4.66 ±0.18 |

Note. — Na⁺, and K⁺ values reported as milliequivalents

The data set forth in Table 1 show that the effectiveness of Compound B begins between 25 and 50 mg./kg. specifically in the form of an enhanced desired sodium excretion with a relatively small potassium excretion. This relationship is reflected in a somewhat higher sodium/potassium quotient. Also Compound C leads, in a concentration of 41 mg./kg. to increased sodium excretion and still less potassium excretion than induced by Compound B.

The combination of Compounds B and C results in a balanced electrolyte excretion (enhanced sodium excretion and small potassium excretion relative to Compounds B and C applied separately). Compound C under these conditions counteracted the excessive potassium excretion induced by higher and longer application of Compound B.

The compositions of this invention are used in diuretic and saluretic applications in a manner known to those skilled in the art. For instance, they may be administered in tablet form, in which a tablet may contain 40–400 milligrams of active substance, or in liquid form in, e.g., 2 milliliters ampules. Typical dosage rates are one tablet per day at the higher active substance/tablet contents or, if no effect is gained, two additional tablets after 6 hours and as needed. Specific use applications and formulations are similar to those for the standard diuretic substance sold under the trademark "Lasix" by Farbwerke Hoechst, AG, Germany.

It will be understood that the specification and examples are illustrative but not limitative of the present invention and that other embodiments within the spirit and scope of the invention will suggest themselves to those skilled in the art.

What is claimed is:

1. A pharmaceutical composition for treating hydropic conditions, comprising diuretically effective amounts of
   a. at least one member of the group consisting of 5-(4-chloro-5-sulfamoyl-2-thenylaminophenyl)-tetrazole and the pharmacologically compatible salts thereof
   b. at least one member of the group consisting of 3-(3-oxo-17β-hydroxy-4,6-androstadien-17β-yl)-propionic acid-γ-lactone and the pharmacologically compatible salts of 3-(3-oxo-17β-hydroxy-4,6-androstadien-17α-yl)-propionic acid,
and a pharmaceutically acceptable carrier.

2. A pharmaceutical composition as claimed in claim 1, comprising 5-(4-chloro-5-sulfamoyl-2-thenylaminophenyl)-tetrazole and 3-(3-oxo-17β-hydroxy-4,6-androstadien-17α-yl)-propionic acid-γ-lactone.

3. A pharmaceutical composition as claimed in claim 1, comprising 5-(4-chloro-5-sulfamoyl-2-thenylaminophenyl)-tetrazole and a pharmacologically compatible salt of 3-(3-oxo-17β-hydroxy-4,6-androstadien-17α-yl)-propionic acid.

4. A pharmaceutical composition as claimed in claim 1, wherein said pharmaceutical carrier is a solid carrier and which also contains pharmaceutically acceptable coloring material.

5. A pharmaceutical composition as claimed in claim 1 in the form of a tablet or dragee.

6. A pharmaceutical composition as claimed in claim 2 comprising about 10 to 100 parts by weight of 5-(4-chloro-5-sulfamoyl-2-thenylaminophenyl)-tetrazole and about 40 parts by weight of 3-(3-oxo-17β-hydroxy-4,6-androstadien-17α-yl)-propionic acid-γ-lactone.

7. A pharmaceutical composition as claimed in claim 6 comprising about 15 to 30 parts by weight of 5-(4-chloro-5-sulfamoyl-2-thenylaminophenyl)-tetrazole and about 40 parts by weight of 3-(3-oxo-17β-hydroxy-4,6-androstadien-17α-yl)-propionic acid-γ-lactone.

8. A pharmaceutical composition as claimed in claim 3 comprising about 10 to 50 parts by weight of 5-(4-chloro-5-sulfamoyl-2-thenylaminophenyl)-tetrazole and about 200 parts by weight of a salt of 3-(3-oxo-17β-hydroxy-4,6-androstadien-17α-yl)-propionic acid.

9. A pharmaceutical composition as claimed in claim 8 comprising about 15 to 30 parts by weight of 5-(4-chloro-5-sulfamoyl-2-thenylaminophenyl)-tetrazole and about 200 parts by weight of a salt of 3-(3-oxo-17β-hydroxy-4,6-androstadien-17α-yl)-propionic acid.

10. A pharmaceutical composition as claimed in claim 1 wherein the 3-(3-oxo-17β-hydroxy-4,6-androstadien-17α-yl)-propionic acid is in the form of its potassium salt.

11. A pharmaceutical composition as claimed in claim 1 also comprising a liquid pharmaceutical diluent or carrier which is sterile and pyrogen-free.

12. A pharmaceutical composition as claimed in claim 1, wherein said pharmaceutical carrier is a solid carrier which also contains a pharmaceutically acceptable flavoring material.

13. A method for treating a hydropic condition which comprises applying to a subject diuretically effective amounts of a composition as claimed in claim 1.

14. A method as claimed in claim 13 wherein said composition comprises 5-(4-chloro-5-sulfamoyl-2-thenylaminophenyl)-tetrazole and 3-(3-oxo-17β-hydroxy-4-,6-androstadien-17α-yl)-propionic acid-γ-lactone.

15. A method as claimed in claim 13 wherein said composition comprises 5-(4-chloro-5-sulfamoyl-2-thenylaminophenyl)-tetrazole and a pharmacologically compatible salt of 3-(3-oxo-17β-hydroxy-4,6-androstadien-17α-yl)-propionic acid.

16. A method as claimed in claim 13 wherein said carrier is a solid carrier and which also contains pharmaceutically acceptable coloring material.

17. A method as claimed in claim 13 wherein said pharmaceutical carrier is a solid carrier which also contains a pharmaceutically acceptable flavoring material.

18. A method as claimed in claim 13 wherein said composition is in the form of a tablet or dragee.

19. A method as claimed in claim 13 wherein said composition comprises about 10 to 100 parts by weight of 5-(4-chloro-5-sulfamoyl-2-thenylaminophenyl)-tetrazole and about 40 parts by weight of 3-(3-oxo-17β-hydroxy-4,6-androstadien-17α-yl)-propionic acid-γ-lactone.

20. A method as claimed in claim 13 wherein said composition comprises about 15 to 30 parts by weight of 5-(4-chloro-5-sulfamoyl-2-thenylaminophenyl)-tetrazole and about 40 parts by weight of 3-(3-oxo-17β-hydroxy-4,6-androstadien-17α-yl)-propionic acid-γ-lactone.

21. A method as claimed in claim 13 wherein said composition comprises about 10 to 50 parts by weight of 5-(4-chloro-5-sulfamoyl-2-thenylaminophenyl)-tetrazole and about 200 parts by weight of a salt of 3-(3-oxo-17β-hydroxy-4,6-androstadien-17α-yl)-propionic acid.

22. A method as claimed in claim 13 wherein said composition comprises about 15 to 30 parts by weight of 5-(4-chloro-5-sulfamoyl-2-thenylaminophenyl)-tetrazole and about 200 parts by weight of a salt of 3-(3-oxo-17β-hydroxy-4,6-androstadien-17α-yl)-propionic acid.

23. A method as claimed in claim 13 wherein the 3-(3-oxo-17β-hydroxy-4,6-androstadien-17α-yl)-propionic acid is in the form of its potassium salt.

24. A method as claimed in claim 13 wherein the composition also comprises a liquid pharmaceutical diluent or carrier which is sterile and pyrogen-free.

* * * * *